United States Patent [19]

Arenas

[11] Patent Number: 4,834,719
[45] Date of Patent: May 30, 1989

[54] QUICK CONNECT/DISCONNECT TUBING ADAPTER

[75] Inventor: Alvaro E. Arenas, Miami, Fla.

[73] Assignee: Cordis Corporation, Miami, Fla.

[21] Appl. No.: 856,483

[22] Filed: Apr. 28, 1986

[51] Int. Cl.[4] .............................................. A61M 5/00
[52] U.S. Cl. .................... 604/243; 285/178; 604/174; 604/283; 604/905
[58] Field of Search ................... 604/174–180, 604/242–243, 283, 905; 285/178, 382

[56] References Cited

U.S. PATENT DOCUMENTS

| | | | |
|---|---|---|---|
| 3,752,510 | 8/1973 | Windischman et al. | 604/283 X |
| 3,765,420 | 10/1973 | Felczak | 604/180 X |
| 4,287,891 | 9/1981 | Peters | 604/174 |
| 4,323,065 | 4/1982 | Kling | 604/283 |
| 4,580,573 | 4/1986 | Quinn | 604/283 |

FOREIGN PATENT DOCUMENTS

| | | | |
|---|---|---|---|
| 825766 | 12/1959 | United Kingdom | 285/382 |
| 2072288 | 9/1981 | United Kingdom | 285/382 |

Primary Examiner—Dalton L. Truluck
Attorney, Agent, or Firm—Henry W. Collins; Thomas R. Vigil

[57] ABSTRACT

The quick connect/disconnect tubing adapter is used for capturing a tubing within the adapter in a generally sterile manner. The adapter comprises two mating body portions which have passageways for receiving a tubing end portion. A tubing is received in and fixed in the passageways and is adapted to contract around the tubing end portion when the body portions are pulled away from each other. Additionally, a locking mechanism is provided for releasably locking the body portions together in a pulled apart position with the tubing end portion captured in the tubing.

14 Claims, 2 Drawing Sheets

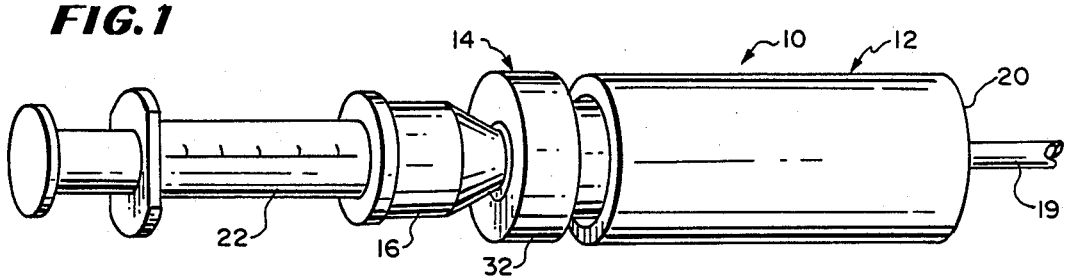
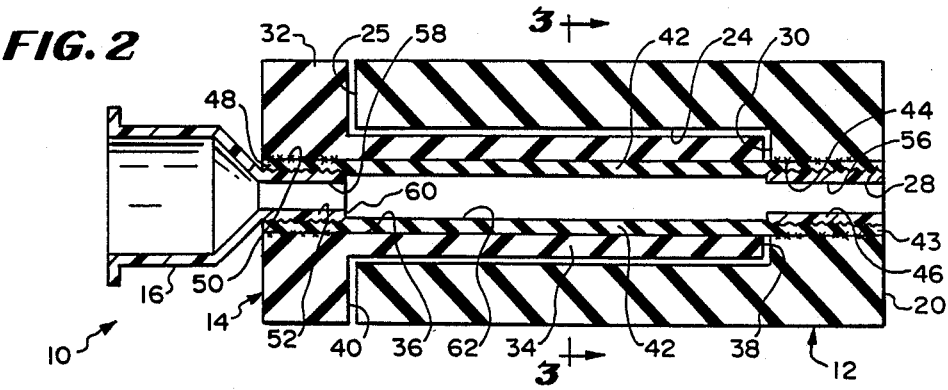
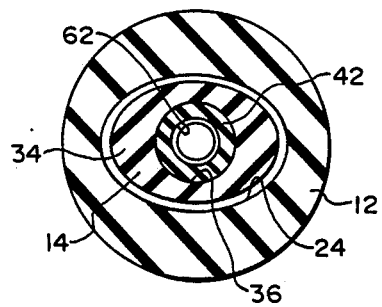
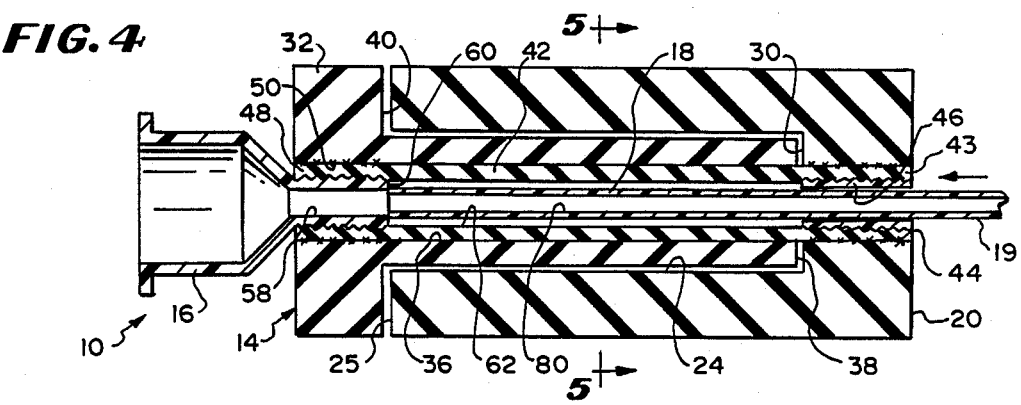
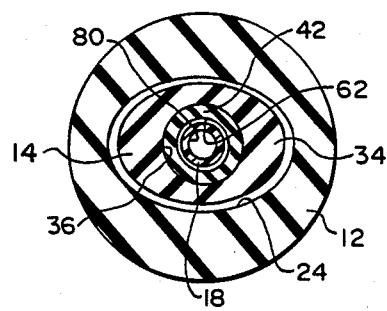

QUICK CONNECT/DISCONNECT TUBING ADAPTER

BACKGROUND OF THE INVENTION

1. Field of the Invention

The present invention relates to an adapter for connecting two sections of tubing together, or in the alternative, to connect a syringe to a tubing. More specifically, the present invention relates to a quick connect/disconnect tubing adapter which provides a large sealing area and is activated, for connection or disconnection, by merely pulling apart two body halves and/or twisting them 90° relative to each other.

2. Description of the Prior Art

Heretofore various tubing adapters have been proposed primarily for use in the field of angiography. Typically, such an angiographic catheter adapter is provided for capturing an end of a tubing and connecting same to a syringe whereby the syringe can be emptied into the catheter tubing in a sterile, bubble-free manner, such as when one is injecting a radio-opaque dye into a patient's body during angiography.

A typical and well known adapter used in this field is known as a Tuey-Borst connector. Such a connector is provided with a rotatable collar and a valve for preventing backflow. However, it is very cumbersome to use inasmuch as a user of this connector requires a "third hand" to use the connector and to open and close a valve in the connector.

Also, special fittings for capturing an end of a tubing are required for this connector and only a particular size of tubing can be used with this connector without modification of the connector.

The use of a quick connect/disconnect tubing adapter constructed according to the teachings of the present invention provides a number of advantages over the Tuey-Borst connector, both in design and use.

First of all, no special fittings for the adapter are required to capture a tubing end in the adapter, and several different sizes of tubing can be accommodated by the same adapter.

Secondly, by placement of two such adapters back-to-back, several tubings of various size can be "spliced" together without modification of the tubing ends.

Also the action required to connect and disconnect the adapter to and from a tubing end is simple and quick, requiring only finger manipulation.

Further, the path formed through the adapter is kept sterile more easily than the path through other adapters such as the Tuey-Borst connector.

The above advantages of the quick connect/disconnect tubing adapter of the present invention will be described in more detail hereinafter in a connector with the description of the preferred embodiment of the adapter of the present invention.

SUMMARY OF THE INVENTION

According to the invention there is provided a quick connect/disconnect tubing adapter for capturing a tubing within the adapter in a generally sterile manner. The adapter comprises two mating body portions which have passageways for receiving a tubing end portion. A tubing is received in and fixed in the passageways and is adapted to contract around the tubing end portion when the body portions are pulled away from each other. Additionally, a locking mechanism is provided for releasably locking the body portions together in a pulled apart position with the tubing end portion captured in the tubing.

BRIEF DESCRIPTION OF THE DRAWINGS

FIG. 1 is a side perspective view of the quick connect/disconnect tubing adapter of the present invention and shows a section of tubing extending out of one end thereof and a hypodermic syringe positioned within a syringe adapter at the other end thereof.

FIG. 2 is a longitudinal sectional view through the adapter of FIG. 1.

FIG. 3 is a cross-sectional view of the tubing adapter and is taken along line 3—3 of FIG. 2.

FIG. 4 is a longitudinal sectional view through the tubing adapter of the present invention and shows the placement of a tubing end portion therein.

FIG. 5 is a cross-sectional view through the tubing adapter of FIG. 4 and is taken along line 5—5 of FIG. 4.

DESCRIPTION OF THE PREFERRED EMBODIMENT

Figure 6:
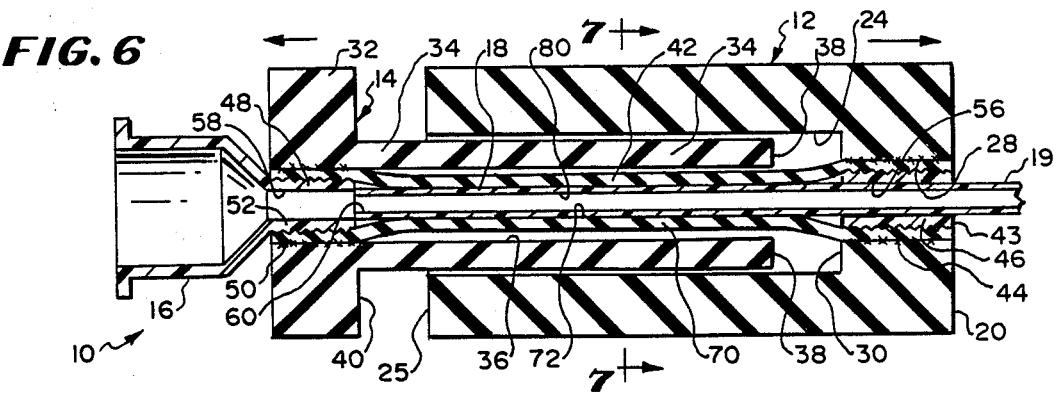
FIG. 6 is a longitudinal sectional view through the tubing adapter with two body portions thereof being pulled apart to cause a tubing connected between the two body portions to squeeze against and capture the tubing end portion.

Referring now to the drawings in greater detail, there is illustrated in FIG. 1 a quick connect/disconnect tubing adapter 10 constructed according to the teachings of the present invention.

As illustrated, the adapter 10 comprises an outer body portion 12 and an inner body portion 14. The inner body portion 14 is provided with a syringe adapter 16 at one end thereof.

In the illustrated embodiment, an end portion 18 (FIG. 4) of a tubing 19 (FIG. 1) is received in the adapter 10 and the tubing 19 is shown in FIG. 1 extending from one end 20 of the body portion 12 of the adapter 10. A syringe barrel 22 is shown mounted within the syringe adapter 16.

Turning now to FIG. 2, which is a longitudinal sectional view through an empty adapter 10, the outer body portion 12 is a generally cylindrical female element having a cavity 24 extending into an opposite end 25 of the body portion 12. A bore 28 extends longitudinally through the body portion 12 from the bottom 30 of the cavity 24 to the end 20.

The inner body portion 14 is a male element which has an annular grippable head portion 32 and smaller-in-cross-section boss 34 which is received in the cavity 24 and which has a through bore or lumen 36. The head portion 32 has an outer diameter which is substantially equal to the outer diameter of the outer body portion 12.

The throughbore or lumen 36 has generally the same diameter as the bore 28 in the outer body portion 12.

The bottom 30 of the cavity 24 forms shoulder 30 in the cavity 24 around the bore 28 and acts as a stop against which an inner end 38 of the boss 34 abuts to limit inward movement of same within the cavity 24.

A further stop 40 is defined by an axially facing annular surface 40 of the head portion 32 adjacent the boss 34 which abuts the end 25 of the body portion 12.

As shown in FIG. 3, the cavity 24 and the boss 34 each have a generally elliptical cross-section with the boss 34 loosely fitting into the cavity 24 such that a longitudinal sliding relationship is provided between the inner body portion 14 and the outer body portion 12.

Figure 9:
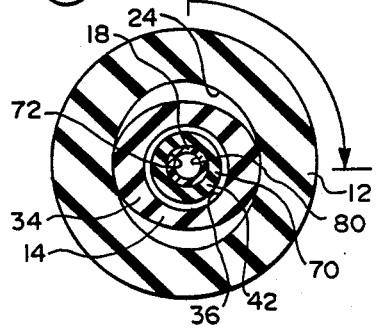
FIG. 9 is a cross-sectional view through the adapter shown in FIG. 8 and is taken along line 9—9 of FIG. 8.

Also the body portions 12 and 14 are made of a plastic material which has some resiliency so that the inner body portion 14 can be rotated within the outer body portion 12 to create a releasable, frictional locking between the body portions 12 and 14 to lock the portions 12 and 14 against relative longitudinal movement therebetween as shown in FIG. 9.

In accordance with the teachings of the present invention, a short piece of flexible tubing 42 is situated in the lumen 36 and in the bore 28 and is fixed at one end 43 in the bore 28 by an adhesive or solvent bonding at 44 and by a threaded or serrated collet 46 screwed or pressed into the end 43 and is fixed at the other end 48 in the lumen 36 by an adhesive or solvent bonding at 50 and by a threaded or serrated nose or sleeve 52 of the syringe adapter 16 which is screwed or pressed into the end 48 as shown in FIG. 2.

The outer diameter of the nose or sleeve 52 and the collet 46 are greater than the inner diameter of the tubing 42 so that an interference, gripping fit is established to firmly hold the tubing 42 in the bores (lumens) 36 and 28.

As will be described in greater detail hereinafter, pulling apart of the body portions 12 and 14 causes stretching and radially inward contraction of the tubing 42 against tubing end portion 18 to provide a capture mechanism of the adapter 10 for capturing tubing end portion 18 therein.

The collet 46 has a bore 56 with a diameter greater than the diameter of a bore 58 in the nose or sleeve 52 of the syringe adapter 16. Also, the nose or sleeve 52 has an annular end surface 60 which serves as a stop for the tubing end portion 18 of tubing 19 inserted therein. Further, the collet 46 serves as a crimp/strain relief sleeve 46.

The syringe adapter 16 is typically provided with a Luer type fitting to lock the syringe barrel 22 in place therein when necessary.

In use, one first secures a syringe barrel 22 within the syringe adapter 16 (FIG. 1). Then one feeds tubing end portion 18 of tubing 19, which may be extending out of a patient's body, into and through the crimp/strain relief sleeve or collet 46, to a position within an initial lumen 62 of the tubing 42 and against the annular stop 60.

In cross-section, as shown in FIG. 5, the tubing end portion 18 is at first loosely received within the lumen 62 of tubing 42.

Then, as illustrated in FIG. 6, once the tubing end portion 18 is positioned in the tubing 42 of the adapter 10, a user grasps outer body portion 12 in one hand and the head portion 32 of inner body portion 14 in the other hand and gently pulls the portions 12 and 14 away from each other.

Such action places a tensile force on the tubing 42 connecting body portions 12 and 14 together and causes the tubing 42 to stretch longitudinally. This lengthwise stretching causes an inward movement or contraction of the tubing 42 in a central unfixed area 70 thereof and a reduction of the diameter of the initial lumen 62 to a reduced-in-diameter lumen 72 in the area 70. This decrease in the luminal diameter of the tubing 42 captures the end portion 18 of the tubing 19 within the stretched tubing 42.

The provision of the collet on crimp/strain relief sleeve 46 eliminates possible disruption of lumen 80 of the tubing end portion 18 of tubing 19 by absorbing stress placed on the tubing end portion 18 by the inward compression of the tubing 42 therearound.

Figure 7:
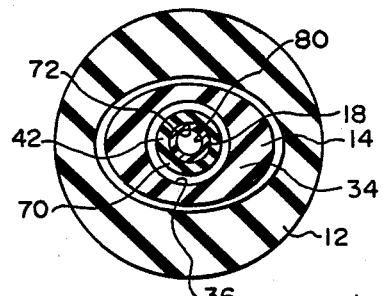
FIG. 7 is a cross-sectional view through the adapter shown in FIG. 6 and is taken along line 7—7 of FIG. 6.

The capture of the tubing end portion 18 is best illustrated in FIGS. 6 and 7 wherein "stretching down" of the inner diameter of the tubing 62 around the outer diameter of the tubing end portion 18 is clearly shown.

Figure 8:
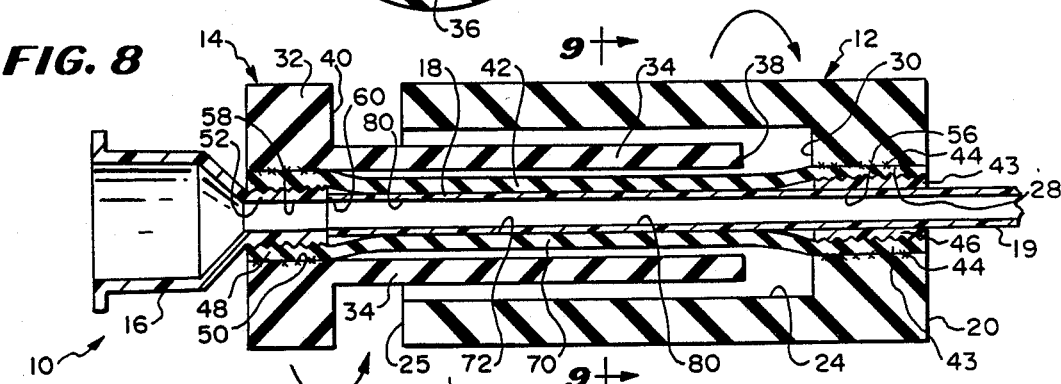
FIG. 8 is a longitudinal sectional view through the adapter and shows the two separated body portions twisted 90° relative to each other.

Then, as illustrated in FIG. 8, one locks the adapter 10 in the capture position by rotating the inner body portion 14 approximately 90° relative to outer body portion 12 causing frictional engagement between the wide cross-section of the boss 34 and the narrow cross-section of the cavity 24.

The mechanism by which the adapter 10 is locked in the capture position is best illustrated in FIG. 9.

When a relative rotation of 90° between outer body portion 12 and inner body portion 14 is accomplished, as illustrated, the wide dimension of the elliptical boss 34 of the inner body portion 14 becomes engaged within the narrow dimension of the elliptical cross-section of cavity 24 of the outer body portion 12 to releasably lock the body portions 12 and 14 in place with tubing 42 stretched and slightly twisted. At the same time, the inward drawing tension of the compressed, and now slightly twisted tubing 42 firmly holds the tubing end portion 18 in the adapter 10.

To release the adapter 10 from engagement with the tubing end portion 18, one merely rotates body portions 12 and 14 relative to each other back to the position shown in FIG. 7 and then releases them to allow them to come toward each other to return to the position shown in FIG. 1.

The adapter 10 also provides a sterile path, since the path is formed literally by a "tube within a tube" capture, with the end of tubing end portion 18 abutting against an inner end 60 of the nose or sleeve 52 of the syringe adapter 16, or, in the alternative, at least within contracted lumen 72 of the tubing 42. Thus, there are no extraneous parts which can leak and contaminate the sterile path from the lumen 80 of the tubing end portion 18 and the interior of the syringe adapter 16.

Figure 10:
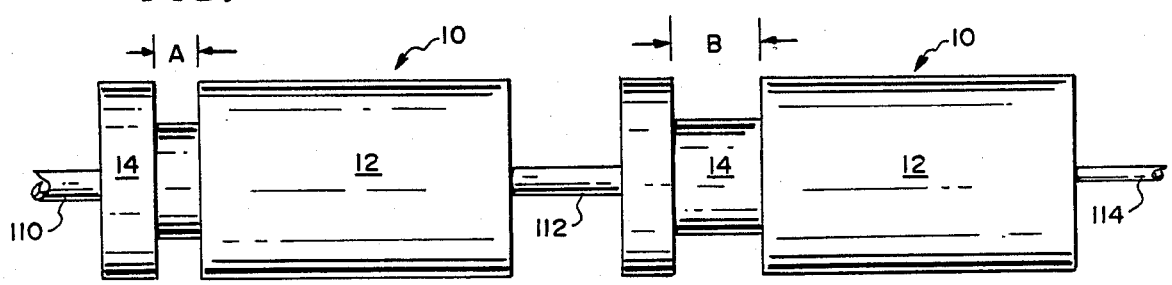
FIG. 10 is a perspective view of two adapters joining three sections of tubing of various diameter.

In FIG. 10, the adapter 10 at the left of the figure shows the portions 12 and 14 separated by a distance A. This slight separation of body portion 12 from body portion 14 is indicative of the positioning of the adapter 10 in a locked, capture position to hold tubing sections 110 and 112 captured therein.

The adapter 10 at the right in FIG. 10, on the other hand, shows the body portions 12 and 14 separated by a distance B which is greater than the distance A. Here, the body portions 12 and 14 are separated to the fullest longitudinal extent possible and are in the "tubing captured, and locked" position for capturing a smaller diameter tubing section 114.

Also, it will be noted that the adapters 10 illustrated here do not have syringe adapters 16. Rather, to adapt each adapter 10 for connecting multiple tubing section 110, 112 and 114, one merely fixes the right hand end of each tubing section 110 and 112 to the tubing 42 in body portion 14 of each adapter 10 shown in FIG. 10.

In summary, the adapter 10 of the present invention is versatile, quickly connected and disconnected, and only requires simple finger manipulation for its use.

The quick connect/disconnect tubing adapter 10 has many advantages some of which have been described above and others of which are inherent in the invention. Also, various modifications can be made to the adapter 10 without departing from the teachings of the invention.

Accordingly, the scope of the invention is only to be limited as necessitated by the accompanying claims.

I claim:

1. A quick connect/disconnect tubing adapter comprising:
   an outer body portion having an elliptically-shaped cavity therein and a bore extending therethrough from the body of said elliptically-shaped cavity to one end of said outer portion;
   an inner body portion, at least a part of which is ellipsoid-shaped and received within said elliptically-shaped cavity, and a part of which extends outwardly from the other end of said outer body portion;
   said inner body portion having a lumen of a diameter generally equal to the diameter of said bore in said outer body portion;
   an elastomeric tubing extending within said lumen inside said inner body portion and within said bore in said outer body portion;
   said tubing being fixed in said lumen of said part of said inner body portion extending outwardly of said outer body portion and in said bore of said outer body portion;
   said tubing having a lumen for receiving a smaller diameter tubing end portion therein;
   said body portions being longitudinally movable away from each other a limited distance to cause said tubing to stretch and contract radially inwardly to capture said tubing end portion therein in a capture position of said body portion; and
   said body portions having means for frictionally locking said body positions in said capture position.

2. The adapter of claim 1 further including a syringe adapter mountable on said outwardly extending portion of said inner body portion.

3. The adapter of claim 2 wherein said syringe adapter includes a Luer type fitting for securing a syringe therein.

4. The adapter of claim 1 wherein said inner and outer body portions are rotatable approximately 90° relative to one another to cause an interference frictional engagement between said body portions, and said elliptical cross sections of said body portions and said rotatability therebetween defining said locking means.

5. The adapter of claim 1 wherein said tubing is bonded to said inner and outer body portions at respective ends thereof.

6. The adapter of claim 1 including a collet received in said tubing in said bore in said outer body portion for clamping said tubing in said bore.

7. The adapter of claim 6 therein said collet has an outer diameter greater than the inner diameter of said tubing.

8. The adapter of claim 7 wherein said outer surface of said collet is serrated or threaded for gripping said tubing in said bore.

9. The adapter of claim 1 including a sleeve which is received in an end portion of said tubing received in said lumen in said inner body portion for clamping said tubing in said lumen.

10. The adapter of claim 9 wherein said sleeve has an outer diameter greater than the inner diameter of said tubing.

11. The adapter of claim 10 wherein said outer surface of said sleeve is serrated or threaded for gripping said tubing in said lumen.

12. The adapter of claim 9 wherein said inner end of said sleeve forms a stop for limiting insertion of a tubing end portion in said tubing.

13. A method for capturing a tubing end portion in the adapter of claim 1 comprising the steps of:
   pulling the inner end and outer body portions apart to cause stretching of said tubing of said adapter to contract around said tubing end portion to capture the tubing end portion in said adapter; and
   rotating the body portions of the adapter approximately 90° relative to each other while they are pulled apart thereby frictionally locking the body portions together with the tubing end portion captured in the adapter.

14. A quick connect/disconnect tubing adapter for capturing a tubing end portion within the adapter in a generally sterile manner, said adapter comprising:
   two elongate mating body portions, one body portion having an out-of-round in cross-section cavity therein and the other body portion having a similar, but smaller, out-of-round in cross-section outer surface along a portion of the length thereof which is received in said cavity;
   passage means in both said body portions of receiving a tubing end portion in both said body portions;
   gripping means extending between said body portions and around a tubing end portion received therein;
   said body portions being movable away from each other to cause said gripping means to grip a tubing end portion received therein; and
   said out-of-round in cross-section cavity in said one body portion and said out-of-round in cross-section outer surface portion of said other body portion defining rotatable means for releasably and frictionally locking said moved apart body portions together upon relative rotation between said body portions with the tubing end portion captured in said gripping means.

* * * * *